United States Patent [19]
Tollini

[11] Patent Number: 4,976,700
[45] Date of Patent: Dec. 11, 1990

[54] MEDICAL SECURING TAPE

[76] Inventor: Dennis R. Tollini, 12 Palmdale Dr., Williamsville, N.Y. 14221

[21] Appl. No.: 476,357

[22] Filed: Feb. 7, 1990

[51] Int. Cl.$^5$ ............................................. A61M 25/02
[52] U.S. Cl. ............................ 604/180; 128/DIG. 26; 128/DIG. 6; 128/877
[58] Field of Search ........ 128/DIG. 6, 877, DIG. 26, 128/DIG. 15; 604/174, 179, 180

[56] References Cited

U.S. PATENT DOCUMENTS

| | | | |
|---|---|---|---|
| 3,288,136 | 11/1966 | Lund | 128/133 |
| 3,430,300 | 3/1969 | Doan | 604/180 X |
| 3,826,254 | 7/1974 | Mellor | 128/133 |
| 3,834,380 | 9/1974 | Boyd | 128/133 |
| 4,165,748 | 8/1979 | Johnson | 128/343 |
| 4,324,237 | 4/1982 | Buttaravoli | 604/180 |
| 4,457,754 | 7/1984 | Buttaravoli | 128/DIG. 26 |
| 4,569,348 | 2/1986 | Hasslinger | 604/179 |
| 4,662,366 | 5/1987 | Tari | 128/877 |
| 4,671,787 | 6/1987 | Widman | 128/DIG. 26 |
| 4,702,736 | 10/1987 | Kalt et al. | 604/180 |
| 4,737,143 | 4/1988 | Russell | 128/DIG. 26 |
| 4,738,662 | 4/1988 | Kalt et al. | 604/180 |
| 4,822,342 | 4/1989 | Brawner | 604/180 |
| 4,838,878 | 6/1989 | Kalt et al. | 604/180 |
| 4,928,712 | 5/1990 | Mele | 128/877 |

FOREIGN PATENT DOCUMENTS 8606640 11/1986 World Int. Prop. O. .......... 604/180

Primary Examiner—Robert A. Hafer
Assistant Examiner—Kevin G. Rooney
Attorney, Agent, or Firm—Joseph P. Gastel

[57] ABSTRACT

A securing tape for securing to a patient's skin or to a support, a medical device such as tubing, a catheter, an intravenous needle, or the like, including an elongated tape having base portions and a central tab formed integrally therewith, pressure-sensitive tape on the base portions and on an exposed window of the tab, and hook and pile fastener portions on opposite sides of the exposed adhesive on the tab and on the base portion facing the exposed adhesive. A method of fabricating a securing tape consisting of the steps of providing a strip of pressure-sensitive tape with release paper thereon, cutting out a window in a central portion of the strip of tape, removing release paper from the central portion of the pressure-sensitive tape, folding the central portion on itself to cause the facing exposed pressure-sensitive adhesive parts to adhere to each other and to provide a window of pressure-sensitive tape defined by the window which was cut out with the remainder of the strip forming a base, and securing hook and pile fastener material on opposite sides of the window of pressure-sensitive tape on the tab and on the portion of the securing tape adjacent thereto which constitutes a base.

17 Claims, 2 Drawing Sheets

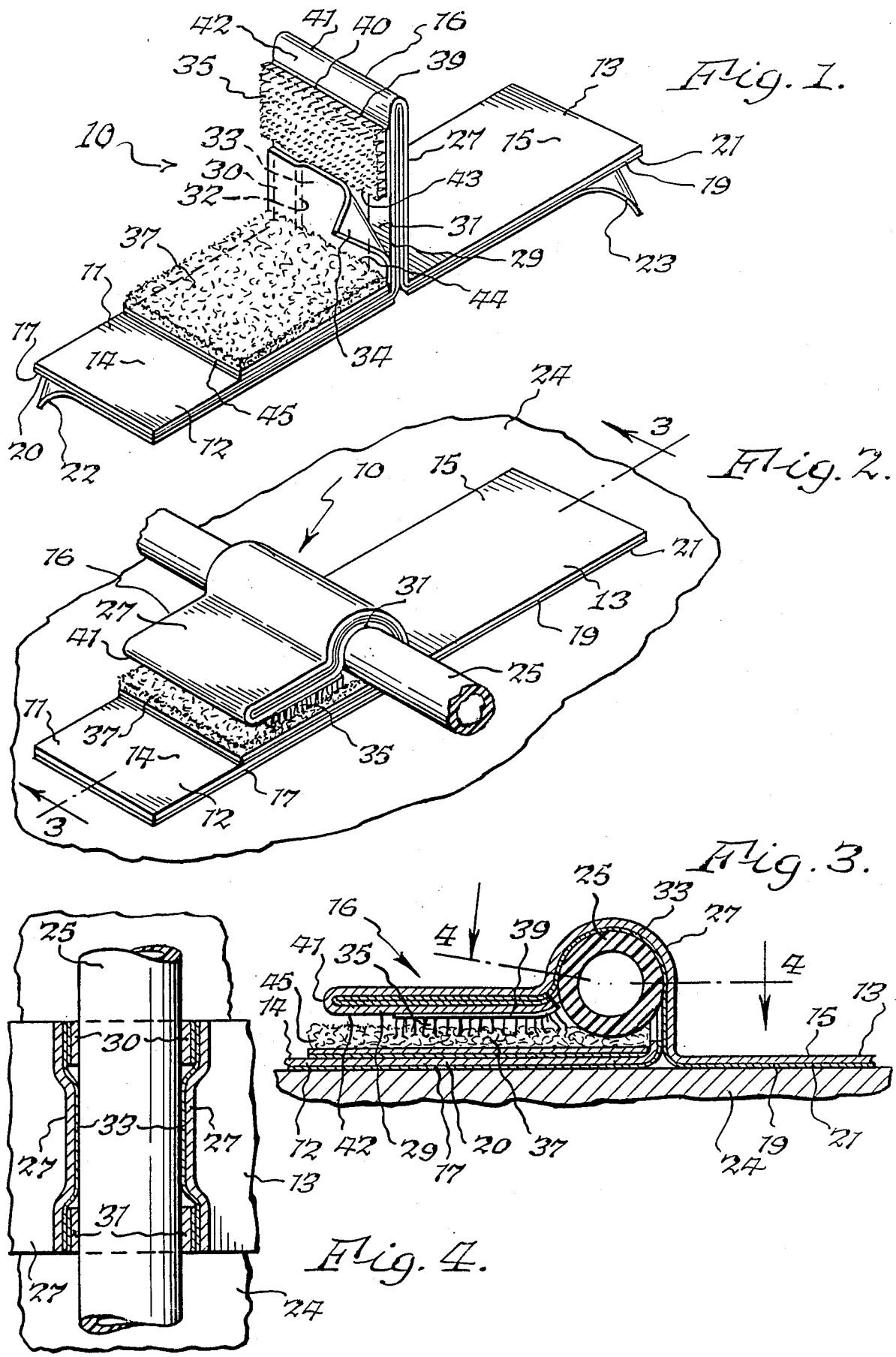

MEDICAL SECURING TAPE

BACKGROUND OF THE INVENTION

The present invention relates to an improved medical securing tape for securing a medical device, such as tubing, a catheter, an intravenous needle, or the like to a patient's skin or to another support.

Securing tapes for use in securing various medical devices to a patient's skin or to a support associated with the patient are well known. Prior securing tapes were either relatively complex and/or difficult to fabricate and/or difficult to use and/or incapable of adjustment once they were installed.

SUMMARY OF THE INVENTION

It is one object of the present invention to provide an improved securing tape for a medical device, such as a tube or catheter, which is extremely simple to use in that it can be applied simply and easily to a patient and will permit the medical device to be installed thereon simply and easily and will positively immobilize the medical device relative to the surface to which it is attached.

Another object of the present invention is to provide a securing tape which permits the medical device mounted thereon not only to be immobilized but also to to be removed and reapplied or readjusted simply and easily and to again be immobilized after it has been so reapplied or readjusted.

A further object of the present invention is to provide an improved securing tape which can be fabricated from conventional materials in a simple and expedient manner. Other objects of the present invention will readily be perceived hereafter.

The present invention relates to a securing tape for securing to a patient's skin or to a support, a medical device such as tubing, a catheter, an intravenous needle, or the like, comprising an elongated tape having an inner surface with pressure-sensitive adhesive thereon and a nonadhesive outer surface, a base portion on said elongated tape for adhesive securement to said patient's skin or to said support, a hold-down tab formed integrally with said base portion and comprising an extension thereof, said hold-down tab comprising facing adhered portions of said inner surface, an exposed portion of said inner surface on said tab, said exposed portion of said inner surface being located so that it is in facing relationship to said nonadhesive outer surface of said base portion to thereby provide adhesive securement with said medical device, and securing means for securing facing portions of said tab and said outer surface of said base portion to each other to secure said tab to said base portion in addition to said adhesive securement between said medical device and said tab.

The present invention also relates to a method of fabricating a securing tape for securing to a patient's skin or to a support, a medical device such as tubing, a catheter or an intravenous needle, or the like, comprising the steps of providing a strip of pressure-sensitive tape with release paper overlying the pressure-sensitive tape surface thereof, cutting an opening in the portion of said pressure-sensitive tape, removing the release paper from a portion of said pressure-sensistive tape proximate said opening, folding the portion of the pressure-sensitive tape from which the release paper was removed back on itself to cover a portion of the exposed pressure-sensitive tape except for the opening to provide a tab while the remainder of said pressure-sensitive tape provides a base, and applying securing means to said pressure-sensitive tape to secure said tabe to said base.

The various aspects of the present invention will be more fully understood when the following portions of the specification are read in conjunction with the accompanying drawings wherein:

BRIEF DESCRIPTION OF THE DRAWINGS

FIG. 1 is a perspective view of the improved securing tape as it is ready for use;

FIG. 2 is a fragmentary perspective view of the securing tape in position on a patient's skin or support and holding a medical device such as a tube;

FIG. 3 is a fragmentary enlarged cross sectional view taken substantially a long line 3—3 of FIG. 2;

FIG. 4 is a fragmentary cross sectional view taken substantially along line 4—4 of FIG. 3;

DESCRIPTION OF THE PREFERRED EMBODIMENTS

Figure 5:
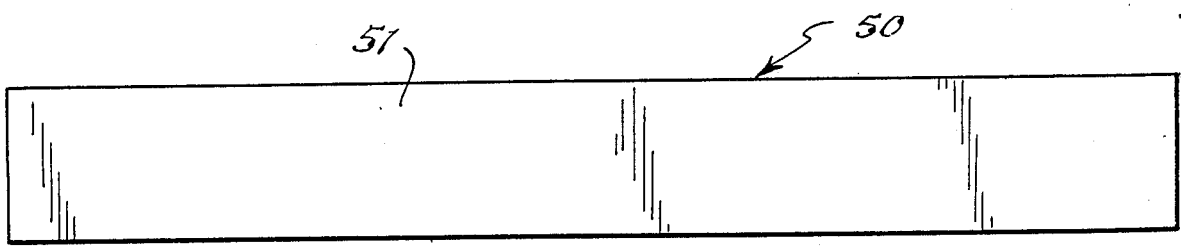
FIG. 5 is a plan view of the first step in the method of fabricating the securing tape of FIGS. 1-4.
Figure 6:
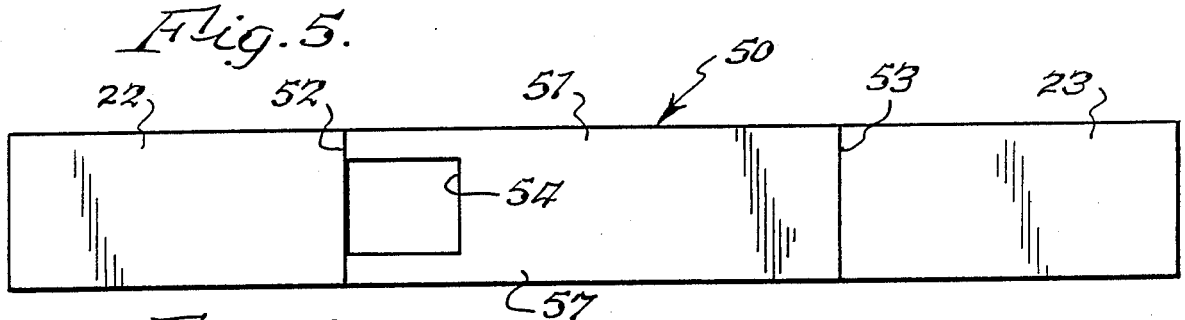
FIG. 6 is a plan view of the second and third steps in the manufacture of the securing tape.
Figure 7:
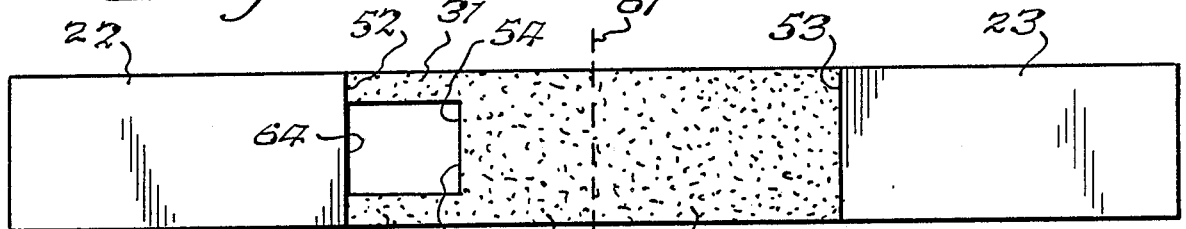
FIG. 7 is a plan view of the third step in the manufacture of the securing tape.

The securing tape 10 of the present invention includes a base portion 11 consisting of spaced parts 12 and 13 and an integral tab 16. Base portions 12 and 13 have outer surfaces 14 and 15, respectively, and inner surfaces 17 and 19, respectively, which have pressure-sensitive adhesive 20 and 21, resepctively, thereon. The adhesive surfaces 20 and 21 are each completely covered by a strip of release paper 22 and 23, respectively, which are peeled off separately to expose the adhesive surfaces 20 and 21 when the base portion 11 is to be adhered to a surface 24 which may be a patient's skin or any other support for a medical device, such as tube 25.

The integral tab 16 extends away from portions 12 and 13 of base portion 11. In this respect, the side 27 of tab 16 is an integral extension of base portion 13 and the side 29 is an integral extension of base portion 14. Sides 27 and 29 are caused to adhere to each other by the adhesive on their inner surfaces, and they are integral continuations of each other by virtue of a return bend at edge 41. More specifically, there are two spaced strips 30 and 31 on tab side 29 which are integral extensions of side 14, and there is a cutout 32 between strips 30 and 31 which exposes the adhesive surface 33 on the surface on the inside of tab side 27. A sheet of release paper 34 adheres to adhesive surface 33 and covers it to prevent it from premature attachment to foreign objects, as is the case with release paper strips 22 and 23.

Hook and pile fabric portions 35 and 37, respectively, which are known under the trademark VELCRO are secured to tab 16 and base portion 12, respectively. In this respect, the hook portion 35 is secured in the position shown in FIG. 1 by its backing 39 of pressure-sensitive adhesive. The edge 40 (FIG. 1) of hook portion 35 falls short of the extreme edge 41 of tabe 16 so as to leave a space 42 which can be grasped digitally to lift the tab from its operating position of FIG. 2 wherein the hook fabric 35 is in engagement with the pile fabric 37. The opposite edge 43 of hook fabric 35 terminates along the edge of exposed adhesive portion 33. The edge 44 of pile fabric 37 is located substantially at the opposite edge of exposed adhesive 33. The opposite edge 45 of pile fabric 37 is positioned as shown.

In use, the release paper 22 and 23 is removed from base portions 12 and 13, respectively, so that the pressure-sensitive adhesive 20 and 21 can be pressed against member 24. Thereafter, the release paper 34 is removed from overlying relationship with adhesive window 33, and the tube 25 or other foreign body is pressed against adhesive surface 33 in window 32 to locate it. Thereafter, tab 16 is folded downwardly from an upstanding position such as shown in FIG. 1 to a securing position such as shown in FIG. 2 to thereby firmly clamp tube 25 in position wherein the adhesive in window 32 positively immobilizes tube 25 against longitudinal or rotational movement. This is of extreme importance not only with a tube which enters a body cavity, but is also of extreme importance if the device 10 is used with an intravenous needle. If for any reason it is desired to reposition tube 25 or possibly place another tube onto securing tape 10, it is merely necessary to open tab 16 by separating the hook and pile fastener portions, remove the original tube 25 and replace it with another tube which is then both held in position by the hook and pile fastener and immobilized by the adhesive in the window. It is to be noted that the relationship between the hook and pile fabric, as shown, permits the securing tape 10 to accommodate tubes 25 of different sizes.

Figure 8:
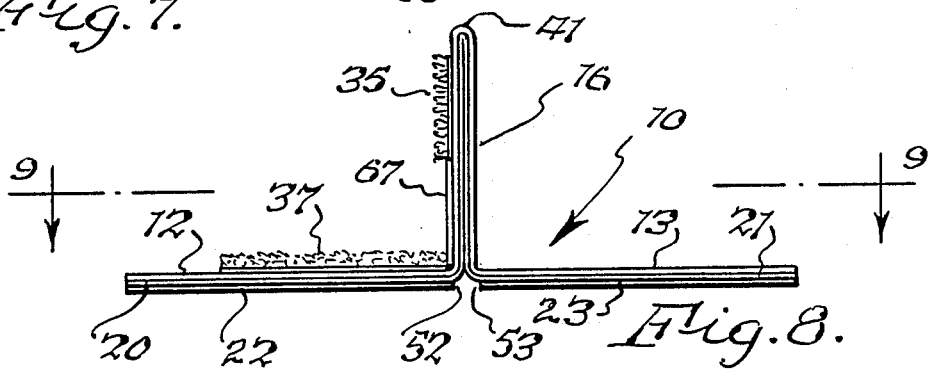
FIG. 8 is a side elevational view showing the fourth and fifth steps in the manufacture of the securing tape.
Figure 9:
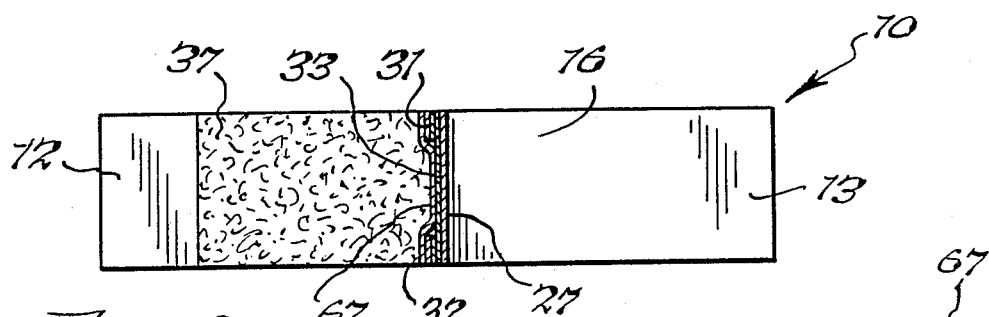
FIG. 9 is a cross sectional view taken substantially along line 9—9 of FIG. 8.
Figure 10:
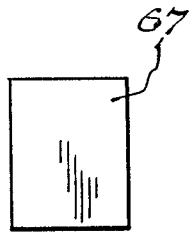
FIG. 10 is a plan view of the protective release paper which is secured to the exposed surface of the adhesive on the tab of the securing tape.

The method of fabricating the securing tape 10 described in FIGS. 1-4 is shown in FIGS. 5-10. The starting portion is a strip 50 of pressure-sensitive tape approximately eight inches long and one inch wide which has a release paper 51 covering its adhesive surface. The first step is to score the release paper 51 along lines 52 and 53. The next step is to cut out a block of the tape 50 adjacent line 52 to provide a window 54. The next step is to remove the release paper 57 between score lines 52 and 53 to expose the adhesive surface 59. Thereafter, the central portion 60 between score lines 52 and 53 is folded about its midpoint line 61 so that the portions of the adhesive surface on opposite sides of fold line 61 stick to each other and thus form tab 16, as shown in FIG. 8. At this time the release paper 22 and 23 adjacent score lines 52 and 53 will still be in covering relationship with the adhesive 20 and 21 on the portions of strip 50 which are now base portions 12 and 13. It can readily be seen that the strips 30 and 31 border cutout 54 and that the edges of cutout 54 are at 64 and 65. The next step is to secure hook portion 35 and pile portion 37 in the positions shown by pressure-sensitive adhesive thereon. The final step in the fabrication is to adhesively secure a release paper patch 67 across the portion of the adhesive surface 59 which is exposed through window or cutout 54.

The securing tape 10 has been depicted in the attitude of FIG. 1 as a matter of convenience for describing it. However, when it is packed for shipment, the parts can either be positioned with the hook and pile fastener portions in engagement with tab 16 lying across base portion 12, or, if desired, tab 16 can be positioned lying against tab portion 13. The tape 50 itself without release paper 51 thereon is approximately 0.007 of an inch thick and the release paper is approximately 0.006 of an inch thick. The material from which the securing tape 10 was fabricated is known under the trademark DUROPORE of the 3M Corporation and it has the grade designation 1538 L. It is a porous pressure-sensitive hypoallergenic tape. It will be appreciated, of course, that other tapes can also be used.

While the preferred embodiment disclosed in the present application has shown the base portion 11 as having two portions 12 and 13 on opposite sides of tab 16, it will be appreciated that the concept of the present invention may also be practiced with a base having only a portion such as 12 facing the exposed adhesive 33 of the tab 16, and in such a configuration, the base portion 13 would be eliminated. The modification of this type is within the scope of the following claims.

While the preferred embodiment has disclosed the use of hook and pile fabric for fastening tab 16 to the base, another method of effecting such fastening is to provide another window of exposed adhesive outwardly on tab 16 from window 32 and this can be used to adhere tab 16 to the nonadhesive surface 14 of base member 12. Furthermore, if desired the additional exposed window of adhesive need not be a separate window but may be an extension of existing window 32.

While preferred embodiments of the present invention have been disclosed, it will be appreciated that it is not limited thereto but may be otherwise embodied with the scope of the following claims.

What is claimed is:

1. A securing tape for securing to a patient's skin or to a support, a medical device such as tubing, a catheter, an intravenous needle, or the like, comprising an elongated tape having an inner surface with pressure-sensitive adhesive thereon and a nonadhesive outer surface, a base portion on said elongated tape for adhesive securement to said patient's skin or to said support, a hold-down tab formed integrally with said base portion and comprising an extension thereof, said hold-down tab comprising facing adhered portions of said inner surface, an exposed portion of said inner surface on said tab, said exposed portion of said inner surface being located so that it is in facing relationship to said nonadhesive outer surface of said base portion to thereby provide adhesive securement with said medical device, and securing means for securing facing portions of said tab and said outer surface of said base portion to each other to secure said tab to said base portion in addition to said adhesive securement between said medical device and said tab.

2. A securing tape as set forth in claim 1 wherein said exposed portion of said inner adhesive surface on said tab is adjacent said base portion, and wherein said securing means comprise cooperating hook and pile fastener means located on opposite sides of said exposed portion.

3. A securing tape as set forth in claim 1 including a portion of said tab extending beyond the portion of said cooperating hook and pile fastener means on said tab for providing a digitally graspable area.

4. A securing tape as set forth in claim 3 wherein said exposed portion of said inner adhesive surface on said tab is adjacent said base portion, and wherein said cooperating hook and pile fastener means are located on opposite sides of said exposed portion.

5. A securing tape as set forth in claim 1 wherein said facing adhered portions of said tab include elongated strip-like portion means adjacent said exposed portion of said inner adhesive surface.

6. A securing tape as set forth in claim 5 wherein said elongated strip-like portion means comprise elongated strips on opposite sides of said exposed portion of said inner adhesive surface.

7. A securing tape as set forth in claim 6 including a portion of said tab extending beyond the portion of said cooperating hook and pile fastener means on said tab for providing a digitally graspable area.

8. A securing tape as set forth in claim 6 wherein said exposed portion of said inner adhesive surface on said tab is adjacent said base portion, and wherein said cooperating hook and pile fastener means are located on opposite sides of said exposed portion.

9. A securing tape as set forth in claim 8 including a portion of said tab extending beyond the portion of said cooperating hook and pile fastener means on said tab for providing a digitally graspable area.

10. A securing tape as set forth in claim 1 wherein said base portion extends on opposite sides of said tab.

11. A securing tape as set forth in claim 1 wherein said cooperating hook and pile fastener means extend outwardly on said base portion and said tab from locations immediately adjacent said exposed portion.

12. A securing tape as set forth in claim 1 including a portion of said tab extending outwardly beyond said securing means for providing a digitally graspable area.

13. A method of fabricating a securing tape for securing to a patient's skin or to a support, a medical device such as tubing, a catheter or an intravenous needle, or the like, comprising the steps of providing a strip of pressure-sensitive tape with release paper overlying the pressure-sensitive tape surface thereof, cutting on opening in a portion of said pressure-sensitive tape, removing the release paper from a portion of said pressure-sensitive tape proximate said opening, folding the portion of the pressure-sensitive tape from which the release paper was removed back on itself to cover a portion of the exposed pressure-sensitive tape except for the opening to provide a tab while the remainder of said pressure-sensitive tape provides a base, and applying securing means to said pressure-sensitive tape to secure said tab to said base.

14. A method as set forth in claim 13 wherein said securing means comprise matable portions of hook and pile fastener members which are applied in facing relationship to said tab and said base on opposite sides of said opening.

15. A method as set forth in claim 13 wherein said release paper is removed from a central portion of said pressure-sensitive tape while permitting release paper to remain on portions of said pressure-sensitive tape on opposite sides of said central portion.

16. A method as set forth in claim 15 wherein said release paper is scored at spaced locations to define the length of said release paper which is removed.

17. A method as set forth in claim 16 wherein the amount of pressure-sensitive tape which is folded back on itself is substantially the entire length of said strip between said spaced locations at which said release paper was scored.

* * * * *